United States Patent [19]

Pfirrmann

[11] Patent Number: 5,819,748
[45] Date of Patent: Oct. 13, 1998

[54] IMPLANT FOR USE IN BONE SURGERY

[75] Inventor: Rolf Wilhelm Pfirrmann, Lucerne, Switzerland

[73] Assignee: Ed Geistlich Sohne AG fur Chemische Industrie, Lucerne, Switzerland

[21] Appl. No.: 283,711

[22] Filed: Aug. 1, 1994

Related U.S. Application Data

[63] Continuation of Ser. No. 974,830, Nov. 16, 1992, abandoned, which is a continuation of Ser. No. 573,294, Sep. 25, 1990, abandoned.

[30] Foreign Application Priority Data

Nov. 30, 1988 [GB] United Kingdom ............... 8827986

[51] Int. Cl.⁶ .......................... A61B 19/00; A61B 17/56
[52] U.S. Cl. ........................ 128/898; 606/60; 606/72
[58] Field of Search .................. 606/76–78, 229, 606/60, 72; 514/2, 21, 222, 801; 424/85.1–85.4, 665; 128/DIG. 8, 898; 623/16

[56] References Cited

U.S. PATENT DOCUMENTS

| | | | |
|---|---|---|---|
| 3,471,598 | 10/1969 | Battista | 128/DIG. 8 |
| 4,066,083 | 1/1978 | Ries | 604/368 |
| 4,233,360 | 11/1980 | Luck et al. | 128/DIG. 8 |
| 4,347,234 | 8/1982 | Wahlig et al. | 606/229 |
| 4,390,519 | 6/1983 | Sawyer | 128/DIG. 8 |
| 4,472,840 | 9/1984 | Jefferies | 623/16 |
| 4,563,350 | 1/1986 | Nathan et al. | 514/21 |
| 4,587,268 | 5/1986 | Pfirrmann | 514/21 |
| 4,604,391 | 8/1986 | Pfirrmann . | |
| 4,642,117 | 2/1987 | Nguyen et al. | 514/21 |
| 4,655,980 | 4/1987 | Chu | 514/21 |
| 4,703,108 | 10/1987 | Siner et al. | 530/356 |
| 4,774,227 | 9/1988 | Piez et al. | 606/76 |
| 4,789,663 | 12/1988 | Wallace et al. | 514/21 |
| 4,795,467 | 1/1989 | Piez et al. | 606/76 |
| 4,837,285 | 6/1989 | Berg et al. | 128/DIG. 8 |
| 4,888,366 | 12/1989 | Chu et al. | 606/76 |
| 4,948,540 | 8/1990 | Nigam | 128/DIG. 8 |
| 4,975,526 | 12/1990 | Kuberasampath et al. | 128/DIG. 8 |
| 5,024,841 | 6/1991 | Chu et al. | 424/85.4 |

FOREIGN PATENT DOCUMENTS 51-66187 6/1976 Japan .
WO 86/07265 12/1986 WIPO .

*Primary Examiner*—Glenn K. Dawson
*Attorney, Agent, or Firm*—Bacon & Thomas

[57] ABSTRACT

A lyophilised collagen sponge used as an implant in osteitis and other bone cavities. The said sponge has dispersed therein antibacterially effective quantities of taurolidine and/or taurultam.

3 Claims, No Drawings

IMPLANT FOR USE IN BONE SURGERY

This application is a continuation of application Ser. No. 07/974,830, filed Nov. 16, 1992, now abandoned, which is a continuation of application Ser. No. 07/573,294, filed Sept. 25, 1990, now abandoned.

This invention relates to a novel collagen-based sponge material for use as an implant in bone surgery.

The treatment of osteomyelitis and osteitis is notoriously difficult. It is necessary to remove all infected bone material and then to induce remodeling, that is re-growth of healthy bone tissue, within the cavity as formed. Unfortunately, re-infection is common and it is necessary that a powerful antibacterial substance is present during the remodeling phase. Remodeling in facio-maxillary surgery and tooth extraction socket filling imposes similar requirements.

In our European Patent No. 48558 we have described resorbable aqueous gels comprising cross-linked gelatin or collagen materials containing antibiotics such as gentamycin or more preferably, taurolidine, for implantation into osteitis cavities. While such gels have proved successful for most purposes, there is a need for alternative implant materials, particularly for implantation into cavities in small bones such as those of the fingers and toes, as well as tooth extraction cavities and other relatively small cavities.

We have now found that a lyophilised sponge of collagen fibres containing the antibacterial substances taurolidine and/or taurultam provide an extremely effective implant material for such uses. Although collagen sponges have been proposed which contain cross-linked or otherwise pre-treated collagen fibres together with an antibiotic such as gentamycin, it has not previously been proposed to impregnate such sponges with taurolidine and taurultam, which have particular advantages in treating bone cavities and bone injuries generally.

According to the present invention we provide a lyophilised collagen sponge for use as an implant in osteitis and other bone cavities, said sponge having dispersed therein antibacterially effective quantities of taurolidine and/or taurultam.

Taurolidine and taurultam are methylol transfer agents which are able to combat not only gram negative and gram positive bacteria but also the exotoxins and endotoxins they produce. They are thus particularly well suited for the treatment of bone cavities liable to re-infection. The soluble collagen sponge according to the invention releases the active substances firstly by diffusion and then by dissolution or resorption of the collagen. The sponge conveniently contains from 1–30 mg/cm$^2$ of taurolidine and/or from 1–60 mg/cm$^2$ taurultam.

Collagen fibres are the most common type of fibres in the connective tissue and the commonest protein in the human body, corresponding to 30% of the total protein. The hyaline cartilage material of the bone consists of 40–45% of collagen fibres. Human bone contains about 40g collagen nitrogen per kg. Collagen fibres consist of collagen fibrils having diameters of 0.2 to 0.5 microns. Their peptide structure contains a high level of proline (12%) and hydroxyproline (10%) residues. Each fibril consists of overlapping molecules of tropocollagen each of which includes a super-helix of 3 polypeptide alpha-chains, which are interwound and stabilised by hydrogen bonding and have terminal non-helical telopeptide sequences.

Four types of collagen are recognised, in which the tropocollagen is built up from three different polypeptide alpha-chains with an average molecular weight of 100,000. The commonest is Type I, occurring for example in skin, muscle, bone, tendons and fascia, which consists of two identical alpha-1-chains and one alpha-2-chain with a different amino acid sequence. Types II, III, and IV consist of three alpha-1-chains which differ in their primary structure in different parts of the body. Type II is the most common collagen type in the hyaline cartilage. Type III occurs inter alia, in the blood vessels and in foetal membranes. Type IV occurs in the basal laminae.

There are significant differences between collagen fibres at different conditions of maturity. Where the connective tissue is in an active phase of fibrillogenesis, for example during growth or wound healing, collagen fractions can be isolated with different properties. The first fraction is extractable by neutral solutions (neutral-soluble collagen); this consists of recently synthesised tropocollagen molecules which are not aggregated or are only beginning to aggregate. The second fraction is extractable by a sodium citrate solution at pH 3.0, and is thus termed the acid-soluble collagen fraction. The third fraction found in older tissues is the insoluble fraction and can only be extracted by very vigorous methods. One basis for the difference between these fractions lies in the degree of cross-linking by oxidation to produce peroxide bridges. Collagen can also be cross-linked chemically via free amino groups, using aldehydes such as formaldehyde or glutaraldehyde or isocyanates such as hexamethylene diisocyanate. By such cross-linking, animal collagen fractions lose their antigenicity almost completely. Cross-linking of collagen fibrils in this way is for example, made use of in heart replacement surgery, where animal, e.g. porcine, valves are conditioned with glutaraldehyde for use as human pulmonary or mitral valve replacements.

In general, it is preferred that the collagen is water insoluble but is rapidly resorbed e.g. within up to 12 hours, for example within 6 to 12 hours. This is compatible with the relatively short half-life of taurolidine and taurultam. Aged or acid soluble collagen may thus be used or, more preferably, neutral soluble collagen fibres may be artificially aged by oxidation, e.g. using a peroxide such as hydrogen peroxide, to form oxygen bridges. Collagen of type I, especially from skin and tendons, advantageously from the flank skin of young calves, is preferred.

However, it may be beneficial to lightly cross-link neutral soluble collagen, e.g. by treatment with a cross-linking agent, for example an aldehyde such as formaldehyde or glutaraldehyde or a isocyanate such as hexamethylene diisocyanate. Such a cross-linked form of collagen will be resorbed more slowly and thus may release the taurolidine or taurultam over a longer period. It is particularly preferred, however, that the level of any cross-linking is much that the collagen is resorbed in 12 hours or less after implantation.

Where the collagen is cross linked it may be beneficial to include an emulsifying agent, during the foaming and lyophilising step e.g. lecithin and/or Cremophor EL (available from BASF), both of which are parenterally acceptable.

Suitable collagen sponge may be obtained commercially, for example from Pentapharm AG of Basel, Switzerland, from Dr. Otto Suwelak GmbH of Billerbeck, West Germany or from Ed Geistlich Söhne A.G. of Wolhusen, Switzerland. Alternatively, such material may be obtained from the appropriate tissues by conventional methods.

Thus, for example, bovine skin, advantageously from young calves, and preferably from the flank region, may be chemically dehaired and mechanically split to separate off the epidermis and the underskin with associated fat. It is important to avoid or minimise contamination with fat. The layer so obtained may be treated with mild alkali, such as calcium hydroxide, e.g. for about 4 weeks. The resulting material may then be acidified, e.g. with 3% hydrochloric acid, washed with running water and comminuted. A proteolytic enzyme may be used to assist separation of collagen from other proteins and a lipase may be used to remove residual fat. However, it is important to avoid antigenic reactions which may result from the use of such enzymes.

The neutral-soluble collagen so produced may then be treated with an oxidising agent such as hydrogen peroxide to form oxygen bridges similar to those formed in the natural aging of collagen.

The comminuted product may then be homogenised with about 7 parts by weight of water, the pH adjusted to about 5.3 and the product further homogenised to produce a foam.

The foamed homogenised material is then filled into cooling cells, e.g. to a depth of about 1.5 cm, rapidly cooled to −20° C. and lyophilised.

The incorporation of the taurolidine or taurultam may be effected either by foaming a collagen solution containing e.g. 2% taurolidine or taurultam, prior to lyophilisation or by redissolving lyophilised collagen in a solution of taurolidine or taurultam and re-lyophilising.

The lyophilised collagen sponge material will normally be sealed in plastic containers and sterilised by radiation e.g. gamma radiation.

Sheets of the collagen sponge according to the invention may be conveniently about 0.5 cm in thickness. Such sheets can be readily cut by the surgeon into small shaped pieces for use as implants. They will normally be laid into the bone cavity without compression. If necessary, spongeosa may also be introduced into the cavity at the same time.

The invention is illustrated by the following nonlimiting Examples. Collagen GN is available from Ed. Geistlich Söhne A.G.

EXAMPLE 1

Collagen GN (a fleecy material containing some collagen fibres, 21×29.8cm =625.8cm$^2$) is soaked with 260g of a 4.8% (w/w) taurolidine solution and then immediately frozen. Freeze-drying gives a compact taurolidine-collagen sponge with 20 mg taurolidine/cm$^2$.

EXAMPLE 2

Collagen GN (21×29.8 cm =625.8cm$^2$) is soaked with 260g of a 4.8% (w/w) taurolidine solution, immediately frozen and then freeze-dried. The dried material is soaked a second time with 130g of a 4.8% (w/w) taurolidine solution and freeze-dried to give a compact taurolidine-collagen sponge with 30 mg taurolidine/cm$^2$.

EXAMPLE 3

Collagen GN (21×29.8 cm =625.8cm$^2$) is soaked with 250g of a 15% taurultam solution and immediately frozen. Freeze-drying gives a compact taurultam-collagen sponge with 60 mg taurultam/cm$^2$.

EXAMPLE 4

Collagen GN (21×29.8 cm =625.8cm$^2$) is soaked with 287.5g of a 13.05% taurultam solution and immediately frozen. Freeze-drying gives a soft taurultam-collagen sponge with 60 mg taurultam/cm$^2$.

EXAMPLE 5

Collagen GN (21×29.8 cm =625.8cm$^2$) is soaked with 537.5g of a 7% taurultam solution and immediately frozen. Freeze-drying gives a soft, downy taurultam-collagen sponge with 60 mg taurultain/cm$^2$.

I claim:

1. In a method for the surgical treatment of a bacterially infected bone cavity with an implant in which the implant is introduced into the bone; wherein the improvement comprises implanting a sponge of uncompressed lyophilised cross-linked collagen into said bacterially infected bone cavity wherein said sponge is cross-linked solely with a physiologically acceptable cross-linking agent dispersed therein; all of said cross linking agent being an antibiotic selected from the group consisting of taurolidine and taurultam with the proviso that said cross-linking agent is the only crosslinking agent present in said sponge: and said cross-linking agent being present in an antibacterially-effective amount.

2. The method of claim 1 wherein said treated bone has an infection caused by a microorganism which infects said bone tissue and said bacterially infected bone cavity is formed by removing substantially all infected( bone tissue from within said bone whereby said bacterially infected bone cavity contains bacteria which is capable of causing re-infection of said bone.

3. The method of claim 2 wherein said infection is selected from the group consisting of osteomyelitis and osteitis.

* * * * *